United States Patent
Ferrera et al.

(10) Patent No.: US 6,242,063 B1
(45) Date of Patent: Jun. 5, 2001

(54) BALLOONS MADE FROM LIQUID CRYSTAL POLYMER BLENDS

(75) Inventors: David A. Ferrera, San Francisco, CA (US); George C. Michaels, Westford; Ralph J. Barry, Hudson, both of MA (US); Lixiao Wang, Maple Grove; Jianhua Chen, Plymouth, both of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 08/926,905

(22) Filed: Sep. 10, 1997

(51) Int. Cl.[7] .................. A61M 25/10; C08L 67/02; C08L 77/00

(52) U.S. Cl. .............. 428/35.2; 428/35.5; 428/36.9; 428/36.91; 428/483; 525/166; 525/179; 604/96.01; 604/103.06; 604/288.01

(58) Field of Search .................. 428/35.2, 35.5, 428/35.7, 36.9, 36.91, 483, 500, 480, 1.33, 1.25; 525/64, 66, 166, 179; 604/96, 93.01, 96.01, 103.06, 288.01

(56) References Cited

U.S. PATENT DOCUMENTS

| Re. 32,983 | 7/1989 | Levy ................ 428/36.92 |
|---|---|---|
| 3,991,014 | 11/1976 | Kleinschuster ............ 260/47 |
| 4,067,852 | 1/1978 | Calundann ................ 260/47 |
| 4,083,829 | 4/1978 | Calundann et al. ........ 260/47 |
| 4,130,545 | 12/1978 | Calundann ................ 260/40 |
| 4,154,244 | 5/1979 | Becker .................... 128/349 |
| 4,161,470 | 7/1979 | Calundann ................ 260/40 |
| 4,318,842 | 3/1982 | East et al. ................. 524/605 |
| 4,331,786 | 5/1982 | Foy et al. ................. 525/408 |
| 4,386,174 | 5/1983 | Cogswell et al. .......... 524/27 |
| 4,433,083 | 2/1984 | Cogswell et al. .......... 524/27 |
| 4,438,236 | 3/1984 | Cogswell et al. .......... 525/165 |
| 4,444,817 | * 4/1984 | Subramanian .......... 428/36 |

(List continued on next page.)

FOREIGN PATENT DOCUMENTS

| 0 369 734 | 5/1990 | (EP) . |
| 0 448 886 A1 | * 12/1990 | (EP) . |
| 92/19316 | 11/1992 | (WO) . |
| 93/24574 | 9/1993 | (WO) . |
| 95/23619 | 9/1995 | (WO) . |
| 96/00752 | 1/1996 | (WO) . |
| 96/04951 | 2/1996 | (WO) . |
| WO 97/24403 | 7/1997 | (WO) . |

OTHER PUBLICATIONS

J. P. deSouza et al., "Processing Studies of In Situ Composites Based on Blends of Liquid Crystalline Polymers With Engineering Thermoplastics", *Polymer Preprints*, 392–393 Apr. 1992.

Q. Lin and A.F. Yee, Measurement of Molecular Orientation of Liquid Crystalline Polymer in situ Composites by X–Ray Scattering Technique, *Polymer Preprints*, pp. 298–299, Apr. 1992.

J. M.Schultz, "Structure Evolution in PET Fibers", *Polymer Preprints*, 304–306 Apr. 1992.

Primary Examiner—Ellis Robinson
Assistant Examiner—John J. Figueroa
(74) Attorney, Agent, or Firm—Vidas, Arrett & Steinkraus

(57) ABSTRACT

Balloons for use on medical devices such as catheter balloons are formed from polymer blend products which include a liquid crystal polymer (LCP), a crystallizable thermoplastic polymer, especially thermoplastic polyesters such as PET, and a compatabilizer. The compatabilizer may be an ethylene-maleic anhydride copolymer, an ethylene-methyl acrylate copolymer, an ethylene-methyl acrylate copolymer, an ethylene-methyl acrylate-maleic anhydride terpolymer, an ethylene-methyl-methacrylic acid terpolymer, an acrylic rubber, an ethylene-ethyl acrylate-glycidyl methacrylate terpolymer or a mixture of two or more such polymers.

12 Claims, 1 Drawing Sheet

U.S. PATENT DOCUMENTS

| | | | |
|---|---|---|---|
| 4,468,364 | 8/1984 | Ide | 264/176 |
| 4,963,313 | 10/1990 | Noddin et al. | 264/573 |
| 5,156,785 * | 10/1992 | Zdrahala | 264/108 |
| 5,195,969 | 3/1993 | Wang et al. | 604/96 |
| 5,264,260 | 11/1993 | Saab | 428/35.5 |
| 5,270,086 | 12/1993 | Hamlin | 428/35.2 |
| 5,290,306 | 3/1994 | Trotta et al. | 606/194 |
| 5,304,340 | 4/1994 | Downey | 264/521 |
| 5,306,246 * | 4/1994 | Sahatijan et al. | 604/96 |
| 5,328,468 | 7/1994 | Kaneko et al. | 604/96 |
| 5,330,428 | 7/1994 | Wang | 604/96 |
| 5,348,538 | 9/1994 | Wang et al. | 604/96 |
| 5,358,486 | 10/1994 | Saab | 604/96 |
| 5,441,489 * | 8/1995 | Utsumi et al. | 604/280 |
| 5,447,497 | 9/1995 | Sogard et al. | 604/101 |
| 5,512,051 | 4/1996 | Wang et al. | 604/96 |
| 5,554,120 | 9/1996 | Chen et al. | 604/96 |
| 5,556,383 | 9/1996 | Wang et al. | 604/96 |
| 5,565,530 | 10/1996 | Hattori et al. | 525/419 |
| 5,587,125 | 12/1996 | Roychowdhury | 264/515 |
| 5,807,327 * | 9/1998 | Green et al. | 604/96 |
| 5,830,182 * | 11/1998 | Wang et al. | 604/96 |
| 5,833,657 * | 11/1998 | Reinhard | 604/96 |

OTHER PUBLICATIONS

J. Liu et al. "Crystal Structure and Transitions in Rigid Rod Thermotropic Liquid Crystal Polymers", *Polymer Preprints*, 337–338 Apr. 1992.

W.J. Farrissey and T.M. Shah, Polyamide Thermoplastic Elastomers, in Handbook of Thermoplastic Elastomers, B.M. Walker and C.R. Rader, eds., pp. 258–281.

R.K. Menon, "Kinetic Theory for Liquid Crystalline Polymer Solutions", *Polymer Preprints*, 574–575 Apr. 1992.

O.V. Noah and N.A. Plate, "Simulation of Macromolecules Conformations in Process of Intra– and Intermolecular Crosslinking", *Polymer Preprints*, 578–579 Apr. 1992.

H. Boublil et al., "Morphology of Polyamid and Polyether Block Amide Blends", *Polymer Engineering and Science*, vol. 29, No. 10, 679–684, May 1989.

E. Okoroafor and J. Rault, "Cryodilation of Thermoplastic PEBA Elastomers", *J. Polymer Sci: Part B: Polymer Physics*, Vopl. 29, 1427–1436, 1991.

E. Barmatov et al., "Oriented Networks of Comb–Shaped Liquid Crystalline Polymers", *Polymer Preprints*, 706–707, Aug. 1993.

M. Brehmer et al., "LC–Elastomers by Chemical and Physical Crosslinking", *Polymer Preprints*, 708–709, Aug. 1993.

A.Y. Bilibin and A.R. Stepanova, "Synthesis of Liquid Crystalline Multiblock Copolymers With Definite Structure of Rigid Block", *Polymer Preprints*, 714–715, Aug. 1993.

Y. Yang et al., Orientation and Strain–Induced Liquid–Crystalline Phase Transition of Networks of Semi–Rigid Chains, *Polymer Preprints*, 729–730, Aug. 1993.

R. Stadler and T. Oehmichen, "Telechelic Oligoaramides — A means for Rigid–Rod Molecular Inforcement of Thermoplastic Materials", *Polymer Preprints*, 731–733, Aug. 1993.

D.H. Weinkauf and D.R. Paul, "The Influence of Molecular Architecture on Gas Transport Properties of Liquid Crystalline Polymers", *Polymer Preprints*, 372–373, Aug. 1991.

P. A. Rodgers and I.C. Sanchez, "Gas Solubility in Polymers and Blends", *Polymer Preprints*, 392–393, Aug. 1991.

W. Brostow; "Properties of Polymer Liquid Crystals: Choosing Molecular Structure and Blending", *Polymer*, vol. 31, 979–995, Jun. 1990.

R. J. Lewis, Sr., "Hawley's Condensed Chemical Dictionary, 12th ed.", pp. 704, 932–934, 936–939, (1993).

Kirk–Othmer Concise Encyclopedia of Chemical Technology, pp. 148–149, 391–395, 814–819, 924–939 (1985).

P. Peyser, "Glass Transition Temperatures of Polymers" in Polymer Handbook 3rd ed. J. Brandrup and E.H. Immergut eds., VI–258–259.

P.J. Collings, "Liquid Crystals, Nature's Delicate Phase of Matter", pp. 20–23, 162–180 (1990).

I.C. Khoo, "Liquid Crystals Physical Properties and Non-linear Optical Phenomena", pp. 5–11, 1995.

B. N. Epstein et al., "Polymer Blends —An Overview", *Polymer Preprints*, 42–43, Jun. 1991.

M.M. Coleman et al., "Miscibility Maps for Copolymer–Copolymer Blends: A Comparison of Theoretical Predicitions to Experimental Data", *Polymer Preprints*, 44–45, Jun. 1991.

W.M. Cheng et al., "Main Chain–Side Chain Liquid Crystal Polymer Blends for Improived Physical Properties", *Polymer Preprints*, 50–51, Jun. 1991.

R.R. Matheson, Jr., "Polymers, Processes and Additives as Systems", *Polymer Preprints*, 52–53, Jun. 1991.

S. Allen et al., "The Effect of Additives on Tensile Properties of PPD–T Fibers", *Polymer Preprints*, 54–55, Jun. 1991.

J.R. Runt et al., "Phase Behavior and Crystallization in Blends of Poly(butyleneterephthalate) and Polyarylate", *Polymer Preprints*, 56–57, Jun. 1991.

T.W. Cheng et al., "Property and Morphology Relationships for Ternary Blends of Polycarbonate, Brittle Polymers, and an Impact Modifier", *Polymer Preprints*, 58–59, Jun. 1991.

M.M. Nir and R.E. Cohen, "Compatibilization of Blends of Crystallizable Polybutadiene Isomers by Precipitation and by Addition of Amorphous Diblock Copolymer", *Polymer Preprints*, 60–61, Jun. 1991.

U. M. Vakil and G.C. Martin, "Analysis of Structure–Property Relations in Crosslinked Epoxies", *Polymer Preprints*, 62–63, Jun. 1991.

Superex Polymer, Inc. press release, "Dual Compatibilized recyclable PET–LCP Alloys with Enhanced Barrier and Structural Performance".

Hoechst Celanese Vectra ® Liquid Crystal Polymer Product Information.

Superex Polymer, Inc Advertisement, "Building product value through new processing and application technologies".

Xydar® product data, Sep. 1994.

Amoco Engineering Plastics for Performance and Value product brochure.

B. Miller, "Rotating Dies Pave Way for Extruding LCP", Plastics World.

A.M. Adur and L.J. Bonis, "PET–LCP Compatibilized Alloys: A New Unique Development".

G.C. Rutledge, "Modelling Chain Rigidity and Orientation in Liquid Crystalline Polymers", *Polymer Preprints*, 537–538 Apr. 1992.

Polymer Science Dictionary, Second Edition, Edited by Alge, pp. 599 and 618, 1997.*

* cited by examiner

BALLOONS MADE FROM LIQUID CRYSTAL POLYMER BLENDS

BACKGROUND OF THE INVENTION

Devices having a balloon mounted at the distal end of a catheter are useful in a variety of medical procedures. A balloon reservoir may be used to deliver a biologically compatible fluid, such a radiologically opaque fluid for contrast x-rays, to a site within the body. Radial expansion of a balloon may be used to expand or inflate a stent positioned within the body. A balloon may also be used to widen a vessel into which the catheter is inserted by dilating the blocked vessel. For example, in the technique of balloon angioplasty, a catheter is inserted for long distances into blood vessels of extremely reduced diameter and used to release or dilate stenoses therein by balloon inflation. These applications require extremely thin walled high strength relatively inelastic balloons of accurately predictable inflation properties.

Depending on the intended use of the balloon and the size of the vessel into which the catheter is inserted, the requirements for strength and size of the balloon vary widely. Balloon angioplasty has perhaps the most demanding requirements for such balloons. The balloons should have uniformly thin walls and a small diameter in their unextended state, since the wall and waist thicknesses of the balloon limit the minimum diameter of the catheter distal end, and therefore determine the limits on minimum blood vessel diameter treatable by this method, as well as the ease of passage of the catheter through the vascular system. High balloon strength is required to enable the balloon to push open a stenosis and to avoid bursting of the balloon under the high internal pressures necessary to inflate the balloon at the site of the stenosis. Sufficient balloon elasticity is required to enable control of the inflated diameter and to allow the surgeon to vary the diameter of the balloon as required to treat individual lesions. To accurately control the balloon diameter, the elasticity of the balloon material must be relatively low. Small variations in pressure must not cause wide variations in balloon diameter.

In the past, PTA catheter balloons have been made from polymeric materials which gave balloons that may be broadly categorized into two groups: a) non-compliant balloons and b) compliant balloons.

Non-compliant balloons typically unfold to a nominal diameter and then stretch or expand only slightly (typically about 5% or less) beyond that diameter as the pressure is increased to burst. See Levy, U.S. Re 32,983, Wang U.S. Pat. No. 5,195,969 and Wang U.S. Pat. No. 5,330,428. All three patents describe biaxially oriented polyethylene terephthalate (PET) balloons. In comparison compliant balloons typically inflate to a nominal diameter and then continue to stretch or expand as the inflation pressure is increased until the strength of the balloon material is exceeded and the balloon bursts, producing a total expansion from nominal diameter to burst of above 5% but generally less than about 80%. See Becker U.S. Pat. No. 4,154,244 and Wang, et al, U.S. Pat. No. 5,556,383.

Balloon characteristics of particular distension and maximum pressure are influenced both by the type of polymer used in forming the balloon and by the conditions under which the balloon is radially expanded. Angioplasty balloons are conventionally made by radially expanding a parison of polymer material at a temperature above its glass transition temperature. For any given balloon material, there will be a range of distensions achievable depending on the conditions chosen for the radial expansion of the balloon.

Balloons have been formed of a wide variety of homopolymer and copolymer materials. The strength characteristics of the balloon may be provided by a single polymer layer or by several layers of polymer material. Balloons with multiple structural polymer layers may be produced by coextrusion, as described in WO 92/19316, U.S. Pat. No. 5,270,086 and U.S. Pat. No. 5,290,306, or by a tube-in-tube technique as described in U.S. Pat. No. 5,512,051; U.S. Pat. No. 5,587,125 and in copending U.S. application Ser. No. 08/611,664 filed Mar. 6, 1996 and PCT/US97/04061, filed Mar. 6, 1997.

In U.S. Pat. No. 5,270,086 it is proposed that a multilayer balloon could be made with an outer layer of a high tensile strength polymer and an inner bonding layer of a highly distensible polymer which had good melt bond and glue adhesion properties. Among the various materials proposed for the outer layer is "liquid crystal polymer". This reference, however, only exemplifies balloons in which the tensile layer is PET and provides no information whatsoever as to what types of liquid crystal polymers may be suitable, or how they may be processed to produce useful balloons.

In U.S. Pat. No. 5,306,246 balloons made of a blend of a crystallizable polymer and an additive that disrupts the crystalline structure are described. Use of liquid crystal polymers as such additives is described.

Various types of liquid crystal polymers are known. One type is a main chain LCP which has an orientational order composed of fairly rigid segments connected together end-to-end by flexible segments. A second type of LCP is a side chain LCP which has an orientational order composed of a single, completely flexible polymer with rigid segments attached along its length by short flexible segments. Nematic, chiral nematic and smectic phases, found in liquid crystals, have been also found in both main chain and side chain LCPs. Nematic LCPs are those in which the rigid sections tend to be oriented along a preferred direction. There is no positional order and the other parts of the LCP display no orientational or positional order. In chiral nematic (or cholesteric) LCPs, the preferred positional direction is not constant but rotates in a helical fashion. In smectic LCPs, the rigid, anisotropic sections of the monomer tend to position themselves in layers as they orient in the liquid crystal phase. Commercial liquid polymers include wholly or partially aromatic polyesters or copolyesters such as XYDAR® (Amoco) or VECTRA® (Hoechst Celanese). Other commercial liquid crystal polymers include SUMIKOSUPER™ and EKONOL™ (Sumitomo Chemical), DuPont HX™ and DuPont ZENITE™ (E.I. DuPont de Nemours), RODRUN™ (Unitika) and GRANLAR™ (Grandmont).

References describing liquid polymers include: U.S. Pat. Nos. 3,991,014, 4,067,852, 4,083,829, 4,130,545, 4,161,470, 4,318,842, and 4,468,364.

LCP polymer blends have been described in U.S. Pat. No. 4,386,174, 4,433,083 and 4,438,236. In U.S. Pat. No. 5,565,530, WO 93/24574 and WO 96/00752 compatibilized blends of liquid polymers are described.

Work by the inventors hereof with commercial liquid crystal polymers and with dry blends of such polymers with PET (i.e. blends produced in extruder by adding the individual polymer components to the extruder hopper) have demonstrated that liquid crystal polymers could not be readily fashioned into balloons for medical devices. Problems encountered included that the extruded tubing was so crystalline that it could not be subsequently blow molded into a balloon and that the extruded polymer was so brittle that the tubes broke up when handled.

To date it has not been suggested to use any type of polymer blend comprising a compatabilized blend of a crystallizable thermoplastic polymer and a liquid crystal polymer in a medical device balloon structure.

SUMMARY OF THE INVENTION

According to the present invention, it has been discovered that certain compatibilized blends of liquid crystalline polymers (LCPs) with crystallizable thermoplastic polymers, especially with polyesters of aromatic diacids, such as PET or PEN, are suitable as medical device balloon materials and can provide unique properties as such.

The LCPs which are useful according to the present invention are characterizable as main chain thermotropic liquid crystal polymers, which may evidence nematic, chiral nematic and smectic phases. The term thermotropic here indicates that these LCPs exhibit the liquid crystal phase as a function of temperature, rather than as a function of pressure on the LCP or as a function of the relative concentration of the LCP. Such LCPs are also suitably those characterized as semi-rigid, anisotropic and highly polarizable LCPs.

The compatabilizer can be a copolymer, such as a block copolymer, including moieties of at least two different chemical structures, respectively providing compatibility with the LCP and with the thermoplastic polymer. The compatibilizer can also be a reactive polymer that reacts with one or both of the LCP and the thermoplastic polymer. It can also be a catalyst that promotes a reaction between the LCP and thermoplastic polymer.

The thermoplastic polymer is preferably selected from polyalkylene terephthalate, polyalkylene naphthalate, and copolyesters thereof, but could be nylon, polyamide, or other material.

Balloons according to the present invention may be formed by a process involving by radial expansion of a small tube or parison under pressure, in which the parison comprises the LCP polymer blend product just described above. The parison can be further coextruded with or have an exterior coating of a relatively soft elastomeric polymer, for instance poly(ester-block-ether) polymers such as HYTREL® (Dupont) and ARNITEL® (DSM); poly(ester-block-ester) polymers such as RITEFLEX® (Hoechst-Celanese); and poly(ester-block-amide) polymers such as PEBAX® (Atochem).

This invention is also a balloon formed by radial expansion of a small tube or parison under pressure, in which the parison comprises a relatively rigid and relatively noncompliant thermotropic main chain LCP. The balloon can be exteriorly coated with or have an exterior layer of a relatively soft elastomeric polymer, such as polyalkylene naphthalate. The LCP has relatively flexible components or thermoplastic short segments within its main chain backbone.

The balloons of the present invention can be used in catheters, such as angioplasty catheters.

DETAILED DESCRIPTION OF PREFERRED EMBODIMENTS

The balloons of the invention may be either single layer balloons, or multilayer balloons. In one preferred embodiment the balloon comprises an inner layer of compatibilized LCP/thermoplastic polyester blend product and an outer layer of a polymer or copolymer.

Figure 1:
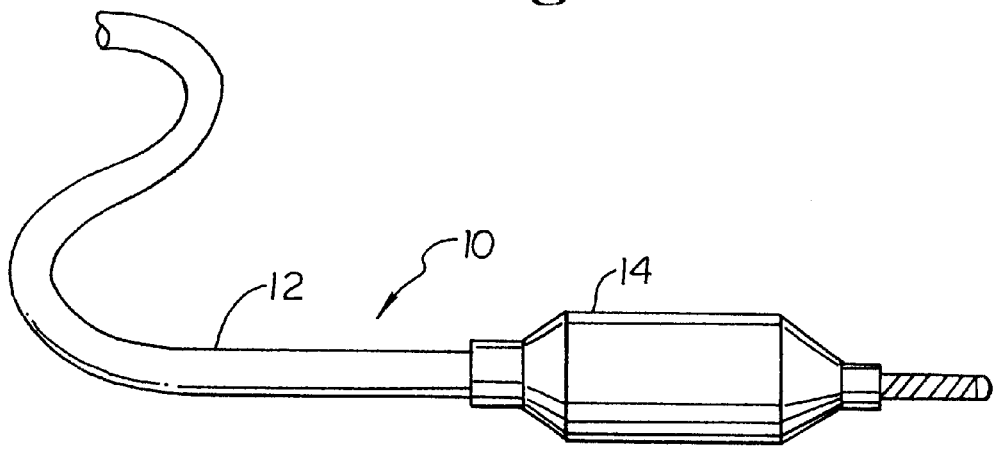
FIG. 1 is a perspective fragmentary view of a balloon catheter having a balloon thereon made in accordance with the invention.

Referring to FIG. 1 there is shown a catheter 10 comprising an elongated tube 12 with a balloon 14, made of a layer of compatibilized LCP polymer in accordance with the invention hereof, mounted at the distal end thereof.

Figure 2:
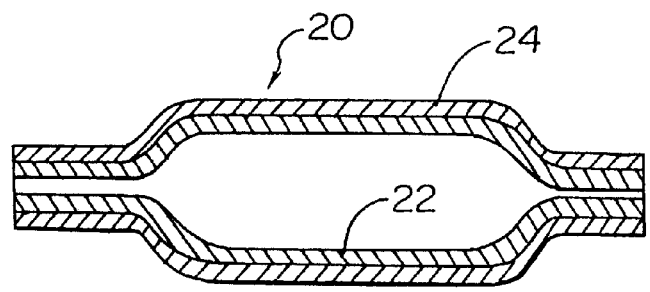
FIG. 2 is a side sectional view of a balloon in accordance with one embodiment of the invention.

Referring to FIG. 2 there is shown a catheter balloon 20 comprising an inner layer 22 of a compatibilized LCP polymer blend product as described herein, and an outer layer 24 of a relatively soft elastomeric polymer such as a poly(ester-block-ether), poly(ester-block-ester) or poly(ester-block-amide).

The thermotropic LCPs used in the polymer blend products used to form the balloons of the invention include wholly or partially aromatic polyesters or copolyesters of an oxycarboxylic acid, optionally with a dicarboxylic acid and a diol. Particularly preferred copolyesters are Xydar®, poly(oxybenzoyl-co-bisphenyl terephthalate) sold by Amoco, and Vectra® A-950, poly (oxybenzoyl-co-oxynaphthoate). Other thermotropic liquid crystal polymers which may be employed in the invention include Sumikosuper™ and EkonoI™ (Sumitomo Chemical), DuPont Zenite™ H™, Rodrun™ (Unitika) and Granlar™ (Grandmont).

Desireably the LCPs used in the present invention have a melt temperature in the range of 250° to 320° C. Preferred LCPs have a melt temperature in the range of 250° to 280° C.

The crystallizable thermoplastic polymers used in the polymer blend products are suitably polyesters or polyamides. Preferred crystallizable thermoplastic polymers are phthalate and napthalate polyesters and copolyesters. Such polymers include polyalkylene terephthalate, such as polyethylene terephthalate and polybutylene terephthalate; polyalkylene terephthalate/isophthalate copolyesters; polyalkylene naphthalate, such as polyethylene naphthalate and polybutylene napthalate; and polyalkylene terephthalate/napthalate copolyesters. Commercially available polyesters and copolyesters include polyethylene terephthalate homopolymers and copolymers such as copolyester Type T74 (Hoechst Celanese); Kodar™ A150 (Eastman Kodak); Cleartuff® 8006, and other polymers sold under the trademarks Cleartuff® or Traytuff® (Shell); and Selar® PT (DuPont). PEN homopolymers and PEN/PETcopolymers include Vituf® SLX by Shell Chemical, PEN homopolymer 14991 sold by Eastman Chemical and various PEN homopolymers and copolymers sold by Teijin Ltd. of Tokyo, Japan under the designations TN8070; TN8060; TN8756T; and TN8880N. Suitable polyamides are nylons 11 and 12.

The compatibilizers include copolyester elastomers; ethylene unsaturated ester copolymers, such as ethylene-maleic anhydride copolymers; copolymers of ethylene and a carboxylic acid or acid derivative, such as ethylene-methyl acrylate copolymers; polyolefins or ethylene-unsaturated ester copolymers grafted with functional monomers, such as ethylene-methyl acrylate copolymers; copolymers of ethylene and a carboxylic acid or acid derivative, such as ethylene-methyl acrylate-maleic anhydride terpolymers; terpolymers of ethylene, unsaturated ester and a carboxylic acid or acid derivative, such as ethylene-methyl acrylate-methacrylic acid terpolymers; maleic acid grafted styreneethylene-butadiene-styrene block copolymers; and acrylic elastomers, such as acrylic rubbers. Similar polymers containing epoxy functional groups, for instance derived from glycidyl methylacylate, in particular, alkyl (meth)acrylate-ethylene-glycidyl (meth)acrylate polymers can also be usefully employed. Ionomeric copolymers can be employed as compatabilizers. Specific suitable compatabilizers include the copolyester elastomer, Hytrel™ HTR-6108 (DuPont); the ethylene-maleic anhydride copolymer, Polybond™ 3009 (BP Chemicals); the ethylene-methyl acrylate copolymer, SP 2205 (Chevron); the ethylene-methyl acrylate copolymer grafted with maleic anhydride, DS 1328/60 (Chevron); the ethylene-methyl acrylate-maleic anhydride terpolymer, Lotader™ 2400; the ethylene-methyl acrylate-maleic acid terpolymers, Escor™ ATX-320, Escor™ ATX-325 or Escor™ XV-11.04; the acrylic rubber, Vamac™ G1 and the ethylene-ethyl acrylate-glycidyl methacrylate terpolymer, Lotader AX 8660.

There are many ways in which LCPs can be blended into thermoplastics according to the present invention. The LCP blend can be a ternary system of LCP, thermoplastic and compatibilizer. Systems with multiple combinations of different LCPs, different thermoplastics and different compatibilizers are also within the scope of this invention. The compatabilizer is designed to modify any phase boundary of the LCP and the thermoplastic polymer and to enhance adhesion between the LCP and the thermoplastic polymer. The compatabilizer can be a block copolymer in which each block of the block copolymer has a different chemical structure and in which at least some of the blocks of the block copolymer have a chemical structure similar to that of the LCP and at least some of the blocks of the block copolymer have a chemical structure similar to that of the thermoplastic polymer. The compatabilizer can also be a coupling agent that reacts with a chain end of the LCP and with a chain end of the thermoplastic polymer, or a catalyst which induces a coupling reaction between chain ends of the LCP and the thermoplastic polymers.

The compatibilized blends may also be a blend of a polyazomethine liquid crystal polymer, a thermoplastic polymer such as a polyamide, and a compatibilizing agent such as E-caprolactam having at least one functional group showing compatability and/or reactivity to the liquid crystal polymer and/or the thermoplastic polmer. Such blends are described in detail in U.S. Pat. No. 5,565,530, the entire contents of which are incorporated herein by reference.

One polymer blend product which may be employed in the present invention comprises PET, a wholly aromatic LCP copolyester and an ethylene-methyl acrylate-acrylic acid terpolymer compatibilizer, for example, Escor™ ATX320, Escor™ ATX-325, or Escor™ XV-11.04. Another suitable polymer blend product comprises PET, a wholly aromatic LCP copolyester and an ethylene-maleic anhydride copolymer compatibilizer such as Polybond™ 3009. Yet other suitable polymer blend products comprise PET, a wholly aromatic LCP copolyester and an ethylene-methyl acrylate copolymer grafted with maleic anhydride compatibilizer, such as DS™ 1328/60, or a copolyester elastomer such as Hytrel™ HTR 6108.

Polymer blend products comprising PET, LCP and at least two compatibilizers, suitably selected from those listed above, are also suitably employed in the practice of the present invention. In particular, the ethylene-methyl acrylate copolymer grafted with maleic anhydride, DS™ 1328/60, and the ethylene-maleic anhydride copolymer, Polybond™ 3009 may be empolyed when the LCP is Vectra®. Also when the LCP is Vectra®, the compatibilizer Polybond™ 3009, and a second compatibilizer selected from Escor™ ATX-320, Escor™ ATX-325, DS1328160™, Escor™ XV-IT.04, or Hytrel®HTR-6108, may be employed.

The properties of the LCP and PET, as well as desired properties of the resulting polymer blend product, are all taken into consideration in selecting suitable compatibilizers for use in the present invention. The properties of the PET/LCP polymer blend products of the present invention are adjusted by adjusting the amount of compatibilizer and, to some extent altering the manner in which the components are combined.

The blend products used in the present invention include from about 0.1 to about 10 weight percent, more preferably from about 0.5 to about 2 percent, thermotropic liquid crystalline polymer. The thermoplastic polyester is utilized in the blend products at a level of from about 40 to about 99 weight percent, preferably from about 85 to about 99 percent. The amount of compatibilizer in the blend products is from about 0.1 to about 30 weight percent, more preferably from about 1 to about 10 weight percent by weight.

The balloons of the invention are particularly suited for use on dilatation catheters used for percutaneous transluminal angioplasty and other minimally invasive procedures. The balloon diameter may be from about 1.5 to about 30 mm, depending on the application to which it is put. The preferred balloons are substantially non-compliant, typically providing a radial expansion of less than 4% when inflation pressure is increased from about 4 atm to about 10 atm.

The compatibilized LCP catheter balloons of this invention are suitably formed to provide a double wall thickness, measured on the uninflated collapsed balloon, of about 0.0002"–0.0020".

In one preferred embodiment of the invention, balloon formation is begun by extruding a tube from a melt of the polymer material. Some initial orientation of the compatibilized LCP is accomplished as the material is drawn down during the extrusion process. This process is typically known as machine orientation and is in the direction of the extrusion operation. It is desirable that the machine orientation be controlled to minimize orientation during extrusion.

Following extrusion, the extruded tube is desirably conditioned at 20–30° C. at a controlled humidity in the range of 10–50% for a period of at least 24 hours. This conditioning provides a constant low moisture level in the tube which prevents hydrolysis and helps to optimize the orientation of the polymer in the subsequent blowing steps.

Principle orientation in the machine and transverse directions may be achieved by heating the tubing to temperatures of 135°–165° C. and physically stretching the extruded homopolymer or random copolymer tube in the axial and radial direction during balloon formation using a free blowing technique. In this step a pressurized gas is applied to the inside of the tubing. The tubing is expanded freely to a specified diameter between cone forms which define the balloon length and cone wall configuration. A similar blowing step is described in U.S. Pat. No. 4,963,313. The blowing pressure and stretching ratio in the machine and transverse directions have a controlling effect on final balloon wall thickness. The axial stretch ratio in this step is suitably from about 2× to about 5×. The radial stretch is suitably from about 3× to about 12×. The tubing diameter to which the balloon is blown in this step is selected so that, after quenching, the inflated but unstressed balloon will have a diameter in the range of about 50–95% of the final diameter desired for the balloon. Suitable inflation pressure for this step are in the range of about 100–180 psi, depending on balloon size. Once the balloon reaches the specified diameter it is quenched to room temperature and depressurized.

The balloon may be finished in a second, mold blow/crystallization, step. In this step the partially formed balloon of the previous step is placed in a mold sized to the final diameter and shape desired for the balloon. The mold is closed and the balloon pressurized to prevent shrinkage, suitably at a pressure of about 5–50 psi. The mold is heated to bring the balloon material to a temperature of about 10–60° C. above the Tg of the balloon material, with pressurization of the balloon sufficient to expand it to the final desired diameter (typically 170–250 psi). This temperature and pressure is held for a brief time, suitably about 5–60 seconds, after which the mold is rapidly quenched to ambient temperature and the balloon removed from the mold.

In another embodiment the balloon is a plural layer laminate including a layer of the compatibilized LCP polymer as described herein and an outer layer of a softer, more elastomeric, polymer to provide improved puncture resistance and to provide a softer less scratchy surface texture to reduce vessel trauma in use. Various techniques are known for producing such multilayer structures, including coextrusion as described in U.S. Pat. No. 5,195,969 (J. Wang, et al.), U.S. Pat. No. 5,290,306 (Trotta et al) and U.S. Pat. No. 5,270,086 (Hamlin), and tube-in-tube techniques as described in copending US application 08/611,664, filed Mar. 6, 1996, U.S. Pat. No. 5,512,051 (J. Wang, et al) and in WO 96/04951 (Schneider Inc.). The higher extrusion, blowing and crystallization temperatures required for the compatibilized LCP polymers used in the invention, however, can make identification of satisfactory outer layer polymers difficult. This is particularly so for coextrusions since the temperature at which the extruder must be heated to melt and extrude the compatibilized LCP polymer melt temperature can exceed the temperature at which many softer compliant thermoplastic polymers begin to thermally degrade. A particularly preferred multilayer laminate structure of the invention is formed from a coextruded tube having an inner layer of a compatibilized LCP polymer blend product as described above and an outer layer of a compatable poly(ester-block-ether) (Hytre® or Arnitel®) or a toughened PET (Selar® PT).

Those skilled in the art will recognize that other techniques known for reparing medical device balloons of other thermoplastic polymer materials can be eadily modified in accordance with the teachings and observations provided herein, and without undue experimentation, to produce balloons according to the present invention.

In addition to structural polymer layers, the balloon may be provided with a nonstructural coating layer, for instance a coating of a lubricious polymer or of a antithrombotic material, to improve surface properties of the balloon.

The following examples illustrate the preparation and unique properties of balloons made from LCP polymer blend products according to the present invention.

EXAMPLES

Compatabilized LCP polymer blend products prepared using a dual compatibilizer system in accordance with WO 96/00552 were obtained from FosterMiller, Inc. at different LCP polymer contents. The crystallizable thermoplastic polymer was Shell Cleartuf 8006, a PET copolyester. A selected polymer blend product was dried by a desiccant hot air dryer using −40° F. dew point air in a plenum style hopper. Polymer moisture was controlled within a range of 10 to 50 ppm by programming drying temperature and time. The polymer blend products were then extruded into tubing in accordance with conventional proceedures for preparing medical balloon parisons. Sizing was accomplished by free extrusion and maintaining constant air pressure inside the tubing while being quenched in a conventional water bath at less than 45° F. Some initial orientation of the homopolymers and copolymers is accomplished as the material is drawn down during the extrusion process. This process is typically known as machine orientation and is in the direction of the extrusion operation. It is important that the machine orientation be controlled to minimize orientation during extrusion.

The extruded tubing was then formed into balloons. Principle orientation in the machine and transverse directions is achieved by heating the tubing within a medium to temperatures of 90° to 110° C. and physically stretching the extruded PET/LCP polymer blend product tube in the axial and radial direction during balloon formation using a blow molding technique in which a pressurized gas is applied to the inside of the tubing. The tubing was expanded freely to a specified diameter. The balloon was then subsequently crystallized by heat setting at a temperature above the blowing temperature to yield the tensile strength and noncompliant property described herein.

Example 1—1% LCP Polymer Blend Product

The products of this example were 5.0 mm diameter balloons. The extruded tubes used had an outside diameter of 0.049" and an inside diameter of 0.026". The balloons were formed at approximately 93° C. with approximately 200 psi of forming pressure. The average balloon burst was 340 psi with a double wall thickness of 0.00152". The average balloon compliance from 4 atm to 12 atm was 1.84%. The average hoops stress of the balloon at burst was 43,113 psi.

Example 2—4% LCP Polymer Blend Product

The products of this example were 5.0 mm diameter balloons. The tubes used had an outside diameter of 0.049" and an inside diameter of 0.026". The balloons were formed at approximately 93° C. with approximately 200 psi of forming pressure. The average balloon burst was 327 psi with a double wall thickness of 0.00155". The average balloon compliance from 4 atm to 12 atm was 1.62%. The average hoops stress of the balloon at burst was 40,931 psi.

Example 3—7% LCP Polymer Blend Product

The products of this example were 5.0 mm balloons. The tubes used had a outside diameter of 0.049" and an inside diameter of 0.026". The balloons were formed at approximately 93° C. with approximately 200 psi of forming pressure. The average balloon burst was 364 psi with a double wall thickness of 0.00152". The average balloon compliance from 4 atm to 12 atm was 1.36%. The average hoops stress of the balloon at burst was 39,560 psi.

Example 4—1% LCP Polymer Blend Product

The product of this sample was a 5.0 mm diameter balloon. The extruded tube used had an outside diameter of 0.049" and an inside diameter of 0.026". The balloon was formed at approximately 93° C. with approximately 200 psi of forming pressure. The balloon was heat set at 140° C. for 60 sec using an inflation pressure of 190 psi. The balloon had a double wall thickness of 0.0014" and had a burst pressure of 490 psi (33.3 atm).

Example 5—1% LCP Polymer Blend Product

The product of this sample was a 5.0 mm diameter balloon. The extruded tube used had an outside diameter of 0.049" and an inside diameter of 0.026". The balloon was formed at approximately 93° C. with approximately 200 psi of forming pressure. The balloon was heat set at 130° C. for 60 sec using an inflation pressure of 200 psi. The balloon had a double wall thickness of 0.0015" and had a burst pressure of 406 psi (27.6 atm).

What is claimed is:

1. A balloon formed from an extruded tubular parison comprising one or more layers of polymeric material, by radial expansion under pressure at an elevated temperature below the lowest temperature which will melt a said layer, wherein the polymeric material of at least one said layer is a polymer melt blend product of a) a thermotropic main-chain liquid crystal polymer (LCP);
   b) a crystallizable thermoplastic polymer; and
   c) at least one compatabilizer for a) and b);
   wherein said at least one compatabilizer modifies any phase boundary of the thermotropic LCP and the crystallizable thermoplastic polymer and also enhances adhesion between said thermotropic LCP and said crystallizable thermoplastic polymer.

2. A balloon as in claim 1 wherein said compatabilizer component c) includes a member selected from the group consisting of maleic acid grafted styrene-ethylene-butadiene-styrene block copolymers, alkyl (meth)acrylate-ethylene-glycidyl (meth)acrylate polymers; copolyester elastomers; ethylene unsaturated ester copolymers; copolymers of ethylene and a carboxylic acid or acid derivative; polyolefins or ethylene-unsaturated ester copolymers grafted with functional monomers; copolymers of ethylene and a carboxylic acid or acid derivative; terpolymers of ethylene, unsaturated ester and a carboxylic acid or acid derivative; ionomeric copolymers; and acrylic elastomers.

3. A balloon as in claim 1 wherein said compatabilizer component c) comprises at least one member selected from the group consisting of ethylene-maleic anhydride copolymers, ethylene-methyl acrylate copolymers, ethylene-methyl acrylate copolymers, ethylene-methyl acrylate-maleic anhydride terpolymers, ethylene-methyl-methacrylic acid terpolymers, acrylic rubbers and ethylene-ethyl acrylate-glycidyl methacrylate terpolymers.

4. A balloon as in claim 1 wherein the crystallizable thermoplastic polymer component b) is selected from polyesters, and polyamides.

5. A balloon as in claim 4 wherein the polyester is selected from the group consisting of alkylene phthalate polyesters, alkylene phthalate copolyesters, alkylene naphthalate polyesters, alkylene naphthalate copolyesters and alkylene phthalate/napthalate copolyesters.

6. A balloon as in claim 1 wherein the thermotropic main-chain liquid crystal polymer component a) is poly(oxybenzoyl-co-bisphenyl terephthalate) or poly(oxybenzoyl-co-oxynaphthoate).

7. A balloon as in claim 6 wherein the crystallizable thermoplastic polymer component b) is polyethylene terephthalate; and the compatabilizer component c) comprises at least one member selected from the group consisting of ethylene-maleic anhydride copolymers, ethylene-methyl acrylate copolymers, ethylene-methyl acrylate copolymers, ethylene-methyl acrylate-maleic anhydride terpolymers, ethylene-methyl-methacrylic acid terpolymers, acrylic rubbers and ethylene-ethyl acrylate-glycidyl methacrylate terpolymers.

8. A balloon as in claim 7 wherein the thermotropic main-chain liquid crystal polymer component a) is utilized in said polymer melt blend product in an amount of from about 0.1 to about 10 weight percent; the crystallizable thermoplastic polymer component b) is utilized in said polymer melt blend product in an amount of from about 40 to about 99 weight percent; and the compatabilizer component c) is utilized in said polymer melt blend product in an amount of from about 0.1 to about 30 weight percent.

9. A balloon as in claim 1 wherein the thermotropic main-chain liquid crystal polymer component a) is utilized in said polymer melt blend product in an amount of from about 0.1 to about 10 weight percent; the crystallizable thermoplastic polymer component b) is utilized in said polymer melt blend product in an amount of from about 40 to about 99 weight percent; and the compatabilizer component c) is utilized in said polymer melt blend product in an amount of from about 0.1 to about 30 weight percent.

10. A balloon as in claim 9 wherein the thermotropic main-chain liquid crystal polymer component a) is utilized in said polymer melt blend product in an amount of from about 0.5 to about 2 weight percent; the crystallizable thermoplastic polymer component b) is utilized in said polymer melt blend product in an amount of from about 85 to about 99 weight percent; and the compatabilizer component c) is utilized in said polymer melt blend product in an amount of from about 1 to about 10 weight percent.

11. A catheter having an inflatable balloon according to claim 1 mounted thereon.

12. A catheter having an inflatable balloon according to claim 9 mounted thereon.

* * * * *